United States Patent [19]

Uchiyama et al.

[11] Patent Number: 4,533,494
[45] Date of Patent: Aug. 6, 1985

[54] PROCESS FOR PURIFYING SECRETIN

[75] Inventors: Mikio Uchiyama, Urawa; Takashi Sato, Tokyo; Hiroshi Yoshino, Abiko; Yutaka Tsuchiya, Tokyo; Masayuki Konishi, Ichinomiya; Masahiko Tsujii, Kagamihara; Yoshihiko Hisatake, Kohnan; Atsushi Koiwa, Gifu, all of Japan

[73] Assignee: Eisai Co., Ltd., Tokyo, Japan

[21] Appl. No.: 465,691

[22] Filed: Feb. 10, 1983

[30] Foreign Application Priority Data

Feb. 15, 1982 [JP] Japan .................................. 57-21311

[51] Int. Cl.$^3$ ............................................ C07C 103/52
[52] U.S. Cl. ............................................. 260/112.5 R
[58] Field of Search ................................ 260/112.5 R

[56] References Cited

PUBLICATIONS

Computer Printout.
Chem. Abstr., vol. 98, (1983) 637m.
Chem. Abstr., vol. 96, (1982) 82112g.
Chem. Abstr., vol. 89, (1978) 110374v.
Biochem. J. (1981) 199, 31-41.
Journal of Chromatography, 153 (1978) 391—398.

*Primary Examiner*—Delbert R. Phillips
*Attorney, Agent, or Firm*—Flynn, Thiel, Boutell & Tanis

[57] ABSTRACT

Purified secretin is obtained by subjecting crude secretin to reversed-phase high-performance liquid chromatography using, as an eluant, a solvent mixture of an acid or salt thereof and an organic solvent.

10 Claims, 2 Drawing Figures

PROCESS FOR PURIFYING SECRETIN

FIELD OF THE INVENTION

The present invention relates to a process for purifying secretin. More particularly, the invention relates to a process for purifying crude secretin in which the purification is effected by reversed-phase high-performance liquid chromatography (HPLC) using a solvent mixture of an acid or a salt thereof and an organic solvent as an eluant. According to the process of the present invention, secretin having a high purity and a high activity can be obtained.

Secretin, which is one of the digestive tract hormones, is a polypeptide consisting of 27 amino acids as shown by the following formula I. It has quite useful pharmacological effects, such as a pancreatic exocrine-accelerating effect, gastrin-stimulating and acid, secretion-inhibiting effects in the stomach, an insulin-liberating effect, a pepsin secretion-stimulating effect and a fat-decomposing effect. It is used as a pancreatic function diagnostic aid and for treatment for duodenal ulcer:

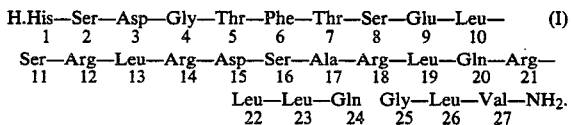

Processes for producing secretin can be divided roughly into two groups. In one of the groups of processes, secretin is extracted from the duodenum of swine or the like. In the other group of processes, secretin is synthesized.

Recently, when secretin is used as a medicine, it is administered intravenously in many cases and, therefore, high purity secretin is demanded in the medical field. However, the above-mentioned processes have the problem that high purity secretin cannot easily be obtained.

Namely, in the former process wherein secretin is extracted from animals, the quantity of the starting material (the duodenum of swine) is limited. Further, the yield is poor and high purity secretin cannot be obtained easily because other peptide hormones are also present in the digestive tracts and impurities are also incorporated therein in the extraction step.

As for the latter process whereby secretin is synthesized, various synthesis processes are considered because secretin is a polypeptide consisting of 27 amino acids. Some of the processes have already been reported [for example, M. Bodanszky et al., J. Am. Chem. Soc., Vol. 90, 4711, (1968)]. A process generally employed in the art, from the viewpoints of operation time, level of significance, yield and cost, comprises synthesizing some protected peptide fragments, condensing them together to obtain a protected heptacosapeptide, removing the protecting groups and purifying the peptide to obtain secretin. In this process, however, it is inevitable that impurities having structures very close to that of secretin are incorporated therein.

Particularly, it is difficult to separate and to remove from secretin a very small amount of optical isomers formed by the racemization in the condensation step of the fragments and impurities formed by the acylation in the step of removing the protecting groups and also by various rearrangement reactions. Further, as pointed out by W. Konig et al. [First International Symposium on Hormonal Receptors in Digestive Tract Physiology. In Serm Symposium No. 3 (1977), Elsevier], even if the purity is apparently enhanced by the purification, the biological activity is reduced in some cases. Also from this viewpoint, it is difficult to obtain secretin having a high purity and high activity.

Thus, there has not been found a satisfactory process for obtaining secretin of a high purity and high activity by purification of crude secretin, although the development of such a process is an important technical problem.

As the main purification processes reported heretofore, there can be mentioned (1) counter-current distribution process [J. Am. Chem. Soc. Vol. 89, p. 6753 (1967)], (2) ion-exchange chromatography with Sp-Sephadex C-25 [Chem. Ber. Vol. 105, p. 2515, (1972)] and (3) chromatography with alkylated dextran gel Sephadex LH-20 (Japanese Patent Laid-Open No. 125165/1977).

However, these processes are as yet unsatisfactory. For example, according to these processes, contaminants having structures similar to those of secretin, such as impurities formed in the protecting group-removing reactions, e.g. the optical isomers, cannot be separated or removed sufficiently. More concretely, ion-exchange chromatography (2) is ineffective for the separation of contaminants having isoelectric points close to that of secretin. Process (3), wherein Sephadex LH-20 is used, is ineffective for the separation of contaminants having molecular weights close to that of secretin. The counter-current distribution process (1) is commercially disadvantageous because it involves a high cost, ion-exchange chromatography should be effected twice in the after-treatment, and a high work load is necessitated.

Secretin purified by these processes has a biological activity of as low as 4,000 cu/mg. Thus, secretin having a high activity cannot be obtained.

After intensive investigations of the purification of secretin for the purpose of obtaining secretin having a high purity and high activity under these circumstances, the inventors have discovered that secretin having a high purity and high activity can be obtained by removing contaminants from crude secretin by reversed-phase high-performance liquid chromatography (HPLC) under specific conditions.

More particularly, the inventors have discovered that the object of the invention can be attained by purifying crude secretin according to the reversed-phase high-performance liquid chromatography process, using a solvent mixture of an acid or salt thereof, and an organic solvent as an eluant. The present invention has been attained on the basis of these discoveries.

The object of the invention is, therefore, to provide a new, easy and industrially practical process for purifying secretin whereby to obtain secretin having a high purity and high activity.

Secretin purified by the process of the invention has a biological activity of at least 5,000 cu/mg, while pure, natural secretin obtained in the prior art had a biological activity of 4,000 cu/mg (as acetate) and 5,000 cu/mg (on dry, free basis) [Gut, 19, 355 (1978)].

In the purification of crude secretin by reversed-phase high-performance liquid chromatography according to the present invention, a solvent mixture of an acid or salt thereof and an organic solvent is used as an eluant. As the acids used in the present invention, there can be mentioned, for example, hydrochloric acid, trifluoroacetic acid, phosphoric acid and perchloric acid. As the salts of these acids, there can be mentioned, for example, sodium phosphate and sodium perchlorate. As the organic solvents, there can be mentioned those used generally, such as acetonitrile ($CH_3CN$), alcohols, e.g. methyl alcohol, ethyl alcohol, isopropyl alcohol, and tetrahydrofuran.

The stationary phase used in the reversed-phase high-performance liquid chromatography according to the present invention is not particularly limited. There can be used, for example, a column packing obtained by chemically bonding an alkyl or cyanopropyl group with silica gel. As the stationary phases available on the market, the following substances can be mentioned: μ-Bondapak C 18 (Waters), Nucleosil C 18 (Nagel), Polygosil C 18 (Nagel), Zorbax C 18 (du Pont), Unisil C 18 (Gas-chro Industry), Unisil Q C 18 (Gas-chro Industry), ODS-HYPE-RSIL (Shadon), SPHERISORB ODS(PS) and TSK-GEL (ODS) (Toyo Soda).

The crude secretin to be purified according to the present invention is not particularly limited. Any low-purity crude secretin material containing contaminants can be used. As typical crude secretin materials, there can be mentioned natural secretin extracted from the duodenum of swine and synthetic secretin.

For the synthesis of secretin, there have been proposed various processes such as the process of M. Bodanszky et al. [J. Am. Chem. Soc. Vol. 90, 4711, (1968)], that of E. Wunsch et al. [Naturwissenschaften Vol. 59, 239 (1972)], that of G. Jager et al. [Chem. Ber. Vol. 107, 215 (1974)], that of H. C. Beyerman et al. [Helv. Chim. Acta, Vol. 59, 1112 (1976)], that of B. Hemmasi [Int. J. Peptide Protein Rec. Vol. 9, 63 (1977)], that of Yauchihara et al. [J. Med. Chem., Vol. 20, 654 (1977)] and Japanese Patent Laid-Open No. 12516/1977. Secretin produced by these processes can be purified according to the present invention as a matter of course. Synthetic secretin produced by any other process can also be purified according to the invention.

According to the inventors' experiments, preferred results were obtained when crude synthetic secretin obtained by removing protecting groups from the following protected secretin was purified:
Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(X)-Leu-Arg(X)-Asp(OBu$^t$)-Ser(Bu$^t$)-Ala-Arg(X)-Leu-Gln-Arg(X)-Leu-Leu-Gln-Gly-Leu-Val-$NH_2$
wherein X represents a group of the formula:

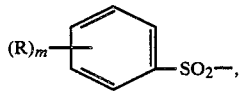

in which R represents an alkyl or alkoxy group having 1 to 3 carbon atoms and m represents an integer of 1 to 3 and when m is 2 or 3, the Rs can be the same or different from each other.

There can be mentioned many processes for producing the above-mentioned, protected secretin. One of the processes comprises synthesizing three fragments, i.e., fragment A [protected peptide consisting of amino acids 1 to 10 in the above formula [I], i.e., Boc-His(Boc)-Ser(-Bu$^t$)-Asp(OBu$^t$)-Gly-Thr(Bu$^t$)-Phe-Thr(Bu$^t$)-Ser(Bu$^t$)-Glu(OBu$^t$)-Leu-OH], fragment B [protected peptide consisting of amino acids 11 to 17 in the above formula [I], i.e. Z-Ser(Bu$^t$)-Arg(X)-Leu-Arg(X)-Asp(OBu$^t$)-Ser(Bu$^t$)-Ala-OH] and fragment C [protected peptide consisting of amino acids 18 to 27 in the above formula [I], i.e. Z-Arg(X)-Leu-Gln-Arg(X)-Leu-Leu-Gln-Gly-Leu-Val-$NH_2$] separately from one another, then condensing peptide B with peptide C to form a peptide consisting of amino acids 11 to 27 and condensing the resulting peptide with peptide A to obtain protected secretin [II].

When natural secretin, such as one extracted from the duodenum of swine, is to be purified, it is subjected to, for example, gel filtration and/or ion-exchange chromatography to obtain low purity crude secretin still containing foreign proteins after the treatment. This crude secretin is subjected to the process of the present invention to obtain secretin having a high purity and high activity.

The process for purifying crude natural secretin will be described below concretely.

Crude natural secretin having a biological activity of about 1,500 to 2,000 cu/mg, purified by the method of J. Mutt or the method of Tachibana et al. is subjected to reversed-phase high-performance liquid chromatography using, for example, 0.005% hydrochloric acid-/acetonitrile (400/167, V/V) as eluant.

More concretely, a sample of 7 mg secretin/0.9 ml eluate is poured into a reversed-phase column and the elution is effected with 0.005% hydrochloric acid-/acetonitrile (400/167, V/V) at a rate of 8 to 9 ml/min to take a secretin peak fraction. Preferred results are obtained when said 0.005% hydrochloric acid/acetonitrile is used as the eluant. When this eluant is used, impurities having an elution time close to that of the secretin peak fraction are eluted after the elution of secretin, whereby a high yield can be obtained. When 0.5% hydrochloric acid/acetonitrile is used as the eluant, inversion of the elution time of the peak takes place and the yield is reduced.

In the purification of crude synthetic secretin, impurities peculiar to the synthetic secretin, such as those having structures close to that of secretin, can be removed according to the present invention and, accordingly, secretin having a high purity and high activity can be obtained.

The process for purifying crude synthetic secretin will now be described concretely.

Crude synthetic secretin is injected into a reversed-phase column and reversed-phase high-performance liquid chromatography is effected using, for example, hydrochloric acid/acetonitrile as eluant to collect a secretin peak fraction. Preferred results are obtained when 0.5% hydrochloric acid/acetonitrile (400/175, V/V) is used as the eluant. A reason why the acid concentration in the eluant is different from that used for the purification of the crude natural secretin is that the impurities contained in crude synthetic secretin are different from those contained in crude natural secretin. If said acid concentration is employed in the purification of crude synthetic secretin, contaminants, such as optical isomers, can be removed sufficiently and even if a larger amount of the crude secretin is injected therein, the impurities can be separated. In one specific embodiment, a sample (700 mg/12.0 ml eluate) is injected in 100 mg portions and a secretin peak fraction is collected.

The resulting liquid is diluted with water and freeze-dried to obtain secretin hydrochloride having a high purity and activity.

If necessary, the secretin hydrochloride thus obtained can be converted into the corresponding acetate by treatment with an ion exchange resin, such as Amberlite IRA-93, or cation exchange resin, such as CM-Sephadex.

The process of the present invention is distinguished by the advantage that impurities having structures very close to that of secretin, which impurities could not be separated easily in the prior art, can be separated easily in a short time by the reversed-phase high-performance liquid chromatography and that the operations in these steps can be effected at room temperature. Therefore, this process is industrially quite advantageous. The high purity secretin thus obtained has a biological activity of as high as about 5,000 to 6,200 cu/mg (on dry, free basis). Thus, the present invention is highly valuable.

Symbols used in the present description are those generally employed in the peptide chemistry field as shown below:

His: histidine
Ser: serine
Asp: Aspartic acid
Gly: Glycine
Thr: Threonine
Phe: Phenylalanine
Glu: Glutamic acid
Leu: Leucine
Arg: Arginine
Ala: Alanine
Gln: Glutamine
Val: Valine
Boc: tert-Butoxycarbonyl
But: tert-Butyl
OBu$^t$: tert-Butyl ester
Tos: Tosyl
Mts: Mesitylene-2-sulfonyl
Z: Benzyloxycarbonyl

The present invention will now be further described with reference to illustrate examples, which by no means limit the scope of the invention.

EXAMPLE 1

2.32 g of protected secretin (heptacosapeptide) having protecting side chain functional groups and the following formula:

Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$ was dissolved in 50 ml of hydrogen fluoride in a closed hydrogen fluoride reactor in the presence of 4.5 ml of anisole at $-5°$ C. After stirring for one hour, hydrogen fluoride was distilled from the reaction system. The residue was washed with diethyl ether, dissolved in cold water and treated with Amberlite IRA-93 (acetate type) to convert same into the corresponding acetate. It was then freeze-dried to obtain 1.53 g (yield: 88%) of crude secretin in the form of a white powder.

700 mg of the resulting crude secretin was dissolved in 12.6 ml of 0.5% hydrochloric acid/acetonitrile (400/175, V/V) and the solution was subjected to high-performance liquid chromatography by injecting into the column 1.8 ml (100 mg) portions at a flow velocity of 9.0 ml/min using Nucleosil-C$_{18}$ (5$\mu$), (2.0$\phi \times$25 cm) and 0.5% hydrochloric acid/acetonitrile (400/175, V/V). An elution curve at 210 nm UV was prepared. An eluate corresponding to the intended secretin peak fraction was collected. After dilution with water, it was freeze-dried. The resulting powder was dissolved in water. Amberlite IRA-193 (AcOH type) was added to the solution and the mixture was left to stand and then filtered. The filtrate was freeze-dried to obtain 450 mg of secretin having a high purity and high activity, i.e. biological activity of 5,500 cu/mg (as acetate) and 6,100 cu/mg (on dry, free basis) (recovery in amino acid analysis: 90%).

TLC: Rf 0.54 (butanol:acetic acid: pyridine: water=15:5:5:8)

Optical rotation: $[\alpha]_D^{20} = -56.40$ (C=0.4, N-acetate)

Amino acid analysis - found (theory): Asp 1.9(2), Thr 1.9(2), Ser 3.6(4), Glu 2.8(3), Gly 1.9(2), Ala 1.0(1), Val 1.0(1), Leu 6.0(6), Phe 1.0(1), His 0.9(1), Arg. 3.9(4)

Figure 1:
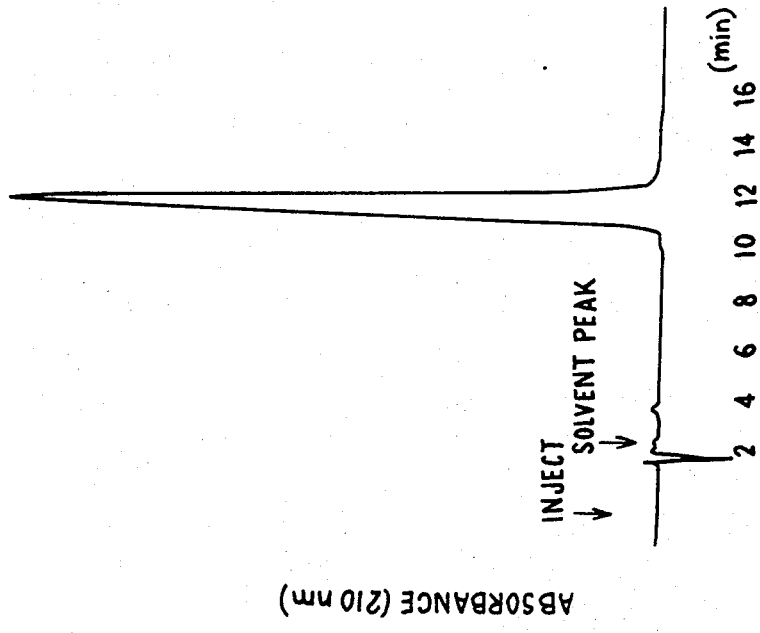
FIG. 1 shows the results of high-performance liquid chromatography of purified secretin obtained in Example 1.

FIG. 1 shows the results of high-performance liquid chromatography of the resulting purified secretin effected under the following conditions:

Column: Nucleosil C$_{18}$ (5$\mu$)
Eluant: 70% HClO$_4$.H$_2$O-MeOH-CH$_3$CN-THF (5:500:275:275:10.5)
Temperature: 30° C.
Flow velocity: 1.0 ml/min

EXAMPLE 2

630 mg of protected secretin (heptacosapeptide) having protecting side chain functional groups and the following formula:

Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Mts)-Leu-Arg(Mts)-Asp(OBu$^t$)-Ser(Bu$^t$)-Ala-Arg(Mts)-Leu-Gln-Arg(Mts)-Leu-Leu-Gln-Gly-Leu-Val-NH$_2$ was dissolved in 10 ml of a mixture of trifluoromethanesulfonic acid and trifluroacetic acid (1:1) in the presence of 0.4 ml of anisole at $-10°$ C. After stirring for one hour, diethyl ether was added to the solution. The supernatant liquid was removed by decantation. The precipitate was dissolved in cold water and treated with Amberlite IRA-93 (acetate type) to convert the same into the corresponding acetate. It was then freeze-dried to obtain 410 mg (yield: 88%) of crude secretin in the form of a white powder.

600 mg of crude secretin obtained as described above was dissolved in 10.8 ml of 0.5% hydrochloric acid/acetonitrile (400/175, V/V) and the solution was subjected to high-performance liquid chromatography in 1.8 ml portions at a flow velocity of 9.0 ml/min using Nucleosil-C$_{18}$ (5$\mu$) (2.0$\times$25 cm) and 0.5% hydrochloric acid/acetonitrile (400/175, V/V) as eluant. An elution curve at 210 nm UV was prepared. An eluate corresponding to an intended secretin peak fraction was collected. After dilution with water, it was freeze-dried to obtain 370 mg of secretin having a high purity and high activity, i.e. biological activity of 5,400 cu/mg (as acetate) and 6,100 cu/mg (on dry, free basis) (recovery in amino acid analysis: 88%).

TLC: Rf 0.54 (butanol:acetic acid:pyridine:water=15:5:5:8)$_{20}$

Optical rotation: $[\alpha]_D^{20} = -56.0$ (C=0.4, N-acetate)

Amino acid analysis - found (theory): Asp 2.1(2), Thr 2.0(2), Ser 3.8(4), Glu 2.8(3), Gly 1.9(2), Ala 0.9(1), Val 1.0(1), Leu 5.8(6), Phe. 1.0(1), His 1.0(1), Arg. 3.9(4)

EXAMPLE 3

51.7 mg of the crude secretin used in Example 1 was dissolved in 1.2 ml of 3M phosphoric acid/acetonitrile (400/180, V/V). The solution was subjected to high-performance liquid chromatography at a flow velocity of 8.5 ml/min using Nucleosil-$C_{18}$ (5$\mu$) (2.0$\phi\times$25 cm) and 3M phosphoric acid/acetonitrile (400/180, V/V) as eluant. An elution curve at 210 nm UV was prepared. An eluate corresponding to the intended secretin peak fraction was collected. The collected eluate was diluted with water, ioh-exchanged with CM-Sephadex sufficiently buffered with ammonium acetate and freeze-dried to obtain 30 mg of secretin having a high purity and high activity, i.e. biological activity of 5,450 cu/mg (as acetate) and 6,200 cu/mg (on dry, free basis) (recovery in amino acid analysis: 88%).

TLC: Rf 0.54 (butanol:acetic acid:pyridine:-water=15:5:5:8)

Optical rotation: $[\alpha]_D^{20}=-55.8$ (C=0.4, N-acetate)

Amino acid analysis - found (theory): Asp 2.0(2), Thr 2.1(2), Ser 3.9(4), Glu 3.1(3), Gly 2.1(2), Ala 1.1(1), Val 1.0(1), Leu 5.9(6), Phe 0.9(1), His 0.9(1), Arg 3.9(4)

EXAMPLE 4

46 mg of crude natural secretin (biological activity: 1,500–2,000 cu/mg) obtained by purifying secretin extracted from the duodenum of swine according to the method of J. Mutt or the method of Tachibana et al. was dissolved in 6 ml of 0.005% hydrochloric acid/acetonitrile (400/167, V/V) (=7.7 mg/ml). The solution was subjected to high-performance liquid chromatography in 900 $\mu$l portions at a flow velocity of 9 ml/min using Nucleosil-$C_{18}$ (5$\mu$) (2.0$\phi\times$25 cm) and 0.005% hydrochloric acid/acetonitrile (400/167, V/V) as eluant. An elution curve at 210 nm UV was prepared. An eluate corresponding to a secretin peak fraction was collected. After freeze-drying was effected twice, the resulting white powder was dissolved in water and ion-exchanged with Amberlite IRA 93 acetate type resin column. The eluate was freeze-dried to obtain 14.5 mg of natural, pure secretin having a biological activity of 5,450 cu/mg (as acetate) and 6,300 cu/mg (on dry, free basis) (recovery in amino acid analysis: 86.4%).

TLC: Rf 0.54 (butanol:acetic acid:pyridine:-water=15:5:5:8)

Optical rotation: $[\alpha]_D^{20}=-51.9$ (C=0.4, N-acetate)

Amino acid analysis- found (theory): Asp 2.1(2), Thr 2.1(2), Ser 3.8(4), Glu 3.0(3), Gly 1.9(2), Ala 1.0(1), Val 0.9(1), Leu 6.1(6), Phe 0.9(1), His 0.9(1), Arg 4.0(4)

Figure 2:
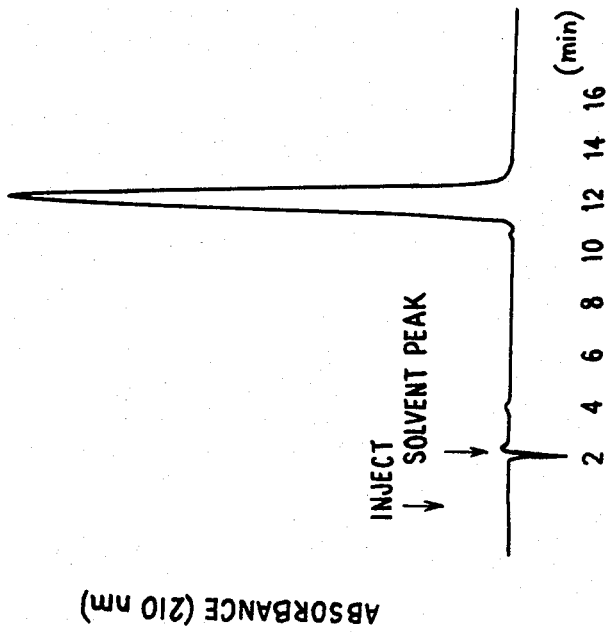
FIG. 2 shows the results of high-performance liquid chromatography of purified secretin obtained in Example 4.

FIG. 2 shows the results of high-performance liquid chromatography of purified secretin obtained as above. The conditions were the same as in Example 1.

The embodiments of the invention in which an exclusive property or privilege is claimed are defined as follows:

1. A process for purifying crude secretin selected from the group consisting of synthetic crude secretin and natural crude secretin, which comprises subjecting the crude secretin to reversed-phase, high-performance, liquid chromatography using, as an eluant, a solvent mixture of (1) an aqueous solution of a substance selected from the group consisting of hydrochloric acid, trifluoroacetic acid, phosphoric acid, perchloric acid, sodium phosphate and sodium perchlorate, and (2) a polar organic solvent which is miscible with water and is selected from the group consisting of acetonitrile, methyl alcohol, ethyl alcohol, isopropyl alcohol and tetrahydrofuran, and using, as a stationary phase, column packing of silica gel particles having alkyl or cyanopropyl groups chemically bonded thereto, and thereby obtaining a purified secretin having a biological activity of higher than 5000 cu/sq; (as acetate) and higher than 6000 cu/mg (on dry, free basis).

2. A process as claimed in claim 1 in which the stationary phase is column packing of silica gel particles having a $C_{18}$ hydrocarbon chemically bonded thereto.

3. A process as claimed in claim 2 in which the crude secretin is synthetic crude secretin and said eluant is a mixture of 0.5% hydrochloric acid and acetonitrile.

4. A process as claimed in claim 2 in which the crude secretin is natural crude secretin and said eluant is a mixture of 0.005% hydrochloric acid and acetonitrile.

5. A process as claimed in claim 1, wherein said aqueous solution (1) is an aqueous hydrochloric acid solution and said polar organic solvent (2) is acetonitrile.

6. A process as claimed in claim 1, wherein said crude secretin is crude synthetic secretin obtained by removing protecting groups from a protected secretin of the formula:

Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(X)-Leu-Arg(X)-Asp(OBu$^t$)-Ser(Bu$^t$)-Ala-Arg(X)-Leu-Gln-Arg(X)-Leu-Leu-Gln-Gly-Leu-Val-NH$_2$ wherein X represents a group of the formula:

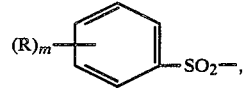

in which R represents an alkyl or alkoxy group having 1 to 3 carbon atoms and m represents an integer of 1 to 3, and when m is 2 or 3, R can be the same or different.

7. A process as claimed in claim 6, wherein said protected secretin has the formula:
Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Tos)-Leu-Arg(Tos)-Asp(OBu$^t$)-Ser(Bu$^t$)-Ala-Arg(Tos)-Leu-Gln-Arg(Tos)-Leu-Leu-Gln-Gly-Leu-Val-NH$_2$.

8. A process as claimed in claim 6, wherein said protected secretin has the formula:
Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(Mts)-Leu-Arg(Mts)-Asp(OBu$^t$)-Ser(Bu$^t$)-Ala-Arg(Mts)-Leu-Gln-Arg(Mts)-Leu-Leu-Gln-Gly-Leu-Val-NH$_2$.

9. A process for purifying a natural or synthetic crude secretin which comprises dissolving said crude secretin in a mixture of (1) an aqueous hydrochloric acid solution and (2) acetonitrile, to form a solution of said crude secretin; then subjecting said crude secretin solution to reversed-phase high-performance liquid chromatography using a column packing of silica gel having alkyl or cyanopropyl adsorbent groups chemically bound thereto as the stationary phase and using said mixture as eluent; then collecting the elute corresponding to a secretin peak fraction, as determined by an elution curve prepared at 210 nm UV; and then freeze-drying the collected secretin to obtain a purified secretin having a biological activity higher than 5,000 cu/mg, as acetate, and higher than 6,000 cu/mg on a dry, free basis.

10. A process as claimed in claim 9, wherein said crude secretin is crude synthetic secretin obtained by removing protecting groups from a protected secretin of the formula:

Boc-His(Boc)-Ser(Bu$^t$)-Asp(OBu$^t$)-Gly-Thr(Bu$^t$)-Phe-Thr(Bu$^t$)-Ser(Bu$^t$)-Glu(OBu$^t$)-Leu-Ser(Bu$^t$)-Arg(X)-Leu-Arg(X)-Asp(OBu$^t$)-Ser(Bu$^t$)-Ala-Arg(X)-Leu-Gln-Arg(X)-Leu-Leu-Gln-Gly-Leu-Val-NH$_2$ wherein X represents a group of the formula:

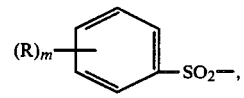

in which R represents an alkyl or alkoxy group having 1 to 3 carbon atoms and m represents an integer of 1 to 3, and when m is 2 or 3, R can be the same or different.

* * * * *

UNITED STATES PATENT AND TRADEMARK OFFICE
CERTIFICATE OF CORRECTION

PATENT NO. : 4 533 494
DATED : August 6, 1985
INVENTOR(S) : Mikio Uchiyama et al It is certified that error appears in the above-identified patent and that said Letters Patent is hereby corrected as shown below:

Column 8, line 11; change "cu/sq;" to ---cu/mg---.

Signed and Sealed this

Twenty-eighth Day of January 1986

[SEAL]

Attest:

DONALD J. QUIGG

Attesting Officer

Commissioner of Patents and Trademarks